United States Patent [19]

Staiger et al.

[11] Patent Number: 4,639,541
[45] Date of Patent: Jan. 27, 1987

[54] SUBSTITUTED PHENYLACETIC ACID IODOPROPARGYL ESTERS, BIOCIDAL AGENTS CONTAINING SAME AND PROCESS FOR MANUFACTURING SAME

[75] Inventors: Gerhard Staiger, Munich; Tassilo Selmayr, Freising; Peter Kinzel, Feldkirchen-Westerham; Anneliese Reütter, Engelharting, all of Fed. Rep. of Germany

[73] Assignee: Consortium für elektrochemische Industrie GmbH, Munich, Fed. Rep. of Germany

[21] Appl. No.: 727,027

[22] Filed: Apr. 25, 1985

[30] Foreign Application Priority Data

May 7, 1984 [DE] Fed. Rep. of Germany ....... 3416722

[51] Int. Cl.$^4$ .................. C07C 79/46; C07C 69/76
[52] U.S. Cl. .................. 560/20; 560/11; 560/51; 560/55; 560/59; 560/81; 558/414; 548/341; 548/262
[58] Field of Search .......... 560/20, 11, 55, 51, 560/59, 81; 558/414; 548/341, 262; 514/532

[56] References Cited

U.S. PATENT DOCUMENTS 4,259,350 3/1981 Morisawa et al. ............. 560/1

FOREIGN PATENT DOCUMENTS 8072540 4/1983 Japan ........................ 170/113

Primary Examiner—Paul J. Killos
Attorney, Agent, or Firm—Collard, Roe & Galgano

[57] ABSTRACT

Substituted phenylactic acid iodopropargyl ester compounds of the general formula:

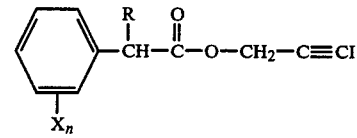

in which R may represent hydrogen, fluorine, chlorine, bromine, iodine, methoxy, 1-imidazolyl or 1,2,4-triazolyl, X represents one or more of the same or different substituents selected from fluorine, chlorine, bromine, iodine, cyano, nitro, carboxyl, an alkyl having from 1 to 12 carbon atoms, an alkoxy having from 1 to 12 carbon atoms, a cycloalkyl having from 3 to 6 carbon atoms, formyl, acetyl, propionyl, benzoyl, phenylsulfonyl, phenyl, phenoxy, and substituted phenyl and phenoxy groups having from 1 to 3 substituents selected from fluorine, chlorine, bromine, nitro, methyl or methoxy, and n is an integer from 1 to 5 and may be zero provided that R does not represent hydrogen. The invention also relates to a process of making the compounds, which are effective ingredients of biocidal agents.

12 Claims, No Drawings

SUBSTITUTED PHENYLACETIC ACID IODOPROPARGYL ESTERS, BIOCIDAL AGENTS CONTAINING SAME AND PROCESS FOR MANUFACTURING SAME

This invention relates to phenylacetic acid iodopropargyl esters, substituted in the phenyl nucleus and/or in the benzyl position.

According to U.S. Pat. No. 4,259,350, phenylacetic acid iodopropargyl ester is already known to be a biocidal agent.

It has now been discovered that a number of phenylacetic acid iodopropargyl esters substituted in the phenyl nucleus and/or in the benzyl position have an increased fungicidal activity. In particular, the compounds according to the present invention are distinguished by a broad spectrum of activity.

More particularly, the invention relates to compounds of the general formula

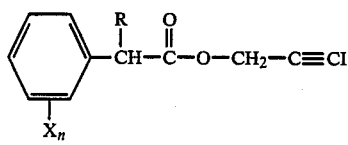

wherein,

R represents hydrogen, fluorine, chlorine, bromine, iodine, methoxy, 1-imidazolyl and 1,2,4-triazolyl;

X represents one or more of the same or different substituents selected from the group consisting of fluorine, chlorine, bromine, iodine, cyano, nitro, carboxyl, alkyl having from 1 to 12 carbon atoms, alkoxy having from 1 to 12 carbon atoms, cycloalkyl having from 3 to 6 carbon atoms, formyl, acetyl, propionyl, benzoyl, phenylsulfonyl, phenyl, phenoxy, and substituted phenyl and phenoxy each having 1 to 3 substituents selected from the group consisting of fluorine, chlorine, bromine, nitro, methyl and methoxy; and is an integer of from 1 to 5, and n, with the proviso that R does not represent hydrogen, can be 0.

Preferably, n is 1, 2, 3 or 4. Where n=1, para-substitution is preferred. Where n=2, o/p-, m/m'- and o/o'- substitutions are preferred. Where n=3, o/o'/p- and o/m/m'- substitutions are preferred. Furthermore, such compounds in which X represents methyl, nitro, chlorine, bromine, iodine or methoxy are preferred. Finally, R is preferably hydrogen, chlorine or bromine.

Examples of especially preferred compounds are:
4-nitrophenylacetic acid iodopropargyl ester;
2-chloro-3,5-dinitrophenylacetic acid iodopropargyl ester;
2,4-dichloro-3,5-dinitrophenylacetic acid iodopropargyl ester;
2,6-dichloro-3,5-dinitrophenylacetic acid iodopropargyl ester;
4-chloro-3,5-dinitrophenylacetic acid iodopropargyl ester;
4-chlorophenylacetic acid iodopropargyl ester;
α-bromo-4-chlorophenylacetic acid iodopropargyl ester;
α-chlorophenylacetic acid iodopropargyl ester; and
2,4,6-trimethylphenylacetic acid iodopropargyl ester.

Further examples of compounds according to the present invention are:
4-methoxyphenylacetic acid iodopropargyl ester;
4-methylphenylacetic acid iodopropargyl ester;
4-ethylphenylacetic acid iodopropargyl ester;
4-iodophenylacetic acid iodopropargyl ester;
4-bromophenylacetic acid iodopropargyl ester;
4-fluorophenylacetic acid iodopropargyl ester;
4-isopropylphenylacetic acid iodopropargyl ester;
4-isopropoxyphenylacetic acid iodopropargyl ester;
4-n-hexylphenylacetic acid iodopropargyl ester;
4-phenylphenylacetic acid iodopropargyl ester;
4-cyclohexylphenylacetic acid iodopropargyl ester;
4-phenoxyphenylacetic acid iodopropargyl ester;
3-phenoxyphenylacetic acid iodopropargyl ester;
2-phenoxyphenylacetic acid iodopropargyl ester;
4-carboxylphenylacetic acid iodopropargyl ester;
1-chlorophenylacetic acid iodopropargyl ester;
2-chlorophenylacetic acid iodopropargyl ester;
2,4-dibromophenylacetic acid iodopropargyl ester;
2,3,6-trichlorophenylacetic acid iodopropargyl ester;
4-cyanophenylacetic acid iodopropargyl ester;
α-(1,2,4-triazolyl)-phenylacetic acid iodopropargyl ester;
α-(1,2,4-triazolyl)-4-chlorophenylacetic acid iodopropargyl ester;
α-imidazolylphenylacetic acid iodopropargyl ester;
α-imidazolyl-4-chlorophenylacetic acid iodopropargyl ester;
4-formylphenylacetic acid iodopropargyl ester;
4-acetylphenylacetic acid iodopropargyl ester; and
4-phenylsulfonylphenylacetic acid iodopropargyl ester.

The compounds according to the invention can be obtained by esterifying 3-iodopropynol with correspondingly substituted phenylacetic acids, or with substituted phenylacetic acid derivatives that will readily react in the esterification reaction.

A preferred process for the manufacture of the compounds according to the invention is characterized in that compounds of the formula

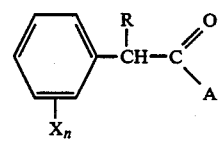

wherein R, X and n have the aforesaid meanings and, further, A represents chlorine, bromine, iodine, acyloxy and alkoxycarbonyloxy, are reacted with 3-iodopropynol in the presence of an acid-binding agent.

Examples of A, where A represents an acyloxy- or an alkoxycarbonyloxy-group, are the 2,2-dimethylpropionyloxy- and benzoyloxy- groups; the methoxycarbonyloxy- and ethoxycarbonyloxy- groups, respectively.

Tertiary amines are especially suitable as acid-binding agents, e.g., triethylamine, dimethylcyclohexylamine and pyridine, among others. Further examples of acid-binding agents are, inter alia, inorganic bases, e.g., sodium hydroxide, potassium hydroxide, calcium oxide, magnesium oxide, sodium carbonate and calcium carbonate.

The reaction temperatures are in the range of from −10° C. to 100° C., especially 20° C. to 60° C.

The reactions are generally carried out in inert solvents, e.g., benzene, toluene, petroleum ether, methylene chloride, chloroform, dioxane, diethyl ether and the like.

Usually, the phenylacetic acid derivative is metered into a mixture of iodopropynol and acid-binding agent at the desired temperature while stirring.

The substituted phenylacetic acids to be used as starting compounds, if not readily available commercially, can be obtained according to methods known to one skilled in the art, e.g., the desired phenylacetic acids may be obtained by reaction of correspondingly substituted benzyl halides with cyanide and subsequent hydrolysis of the benzyl cyanide.

Advantageously, the benzyl cyanides can be obtained by phase transfer-catalyzed reactions of benzyl halides with alkali cyanide solutions in an organic/aqueous two-phase system in the presence of phase transfer catalysts, e.g., quaternary ammonium, phosphonium salts or crown ethers.

The benzyl cyanides are generally hydrolyzed in an acidic medium to the corresponding acid. Only in the case where acid-labile phenyl radicals are present is basic hydrolysis of the cyanide recommended.

For the manufacture of the correspondingly substituted benzyl halides a plurality of synthesizing methods can be applied.

There may be mentioned by way of example, e.g., the known chlorination process of toluene compounds containing corresponding substituents in the benzyl position; the chloromethylation of benzene containing corresponding substituents with hydrogen chloride and formaldehyde in the presence of zinc chloride; or chloromethylation with alpha, alpha'-dichlorodimethyl ether in the presence of concentrated sulfuric acid.

A further method of synthesizing the starting compounds to be used in accordance with the present invention is offered by substitution reactions in phenylacetic acid, especially nitration and acylation. For the nitration reactions, concentrated nitric acid and mixtures of concentrated nitric acid and concentrated sulfuric acid are especially suitable. Often, these reactions are advantageously carried out in the presence of inert diluents, such as, e.g., halogenated hydrocarbons or nitromethane.

Starting compounds to be used in accordance with the invention in which the radical R in the benzyl position is other than hydrogen can be obtained by known methods, e.g., by alpha-chlorination or alpha-bromination of the corresponding phenylacetic acids in accordance with Hell-Volhardt-Zelinski. The resulting phenylacetic acids halogenated in the alpha-position to the carbonyl function are subjected to a further nucleophilic exchange reaction to introduce the substituents fluorine, iodine, methoxy, 1-imidazolyl or 1,2,4-triazolyl. Mandelic acid also can often advantageously be used as a starting compound.

The compounds according to the invention have insecticidal, acaricidal and especially fungicidal activity. They are especially suitable for combating fungal attack in plants or plant products.

The active ingredients according to the invention are distinguished by a broad spectrum of activity and are suitable especially for combating *Botrytis cinerea*, types of alternaria, types of septoria, *Verticillium dahliae, Penicillium glaucum*, types of colletotrichum, types of monilia and types of fusarium. Furthermore, the active ingredients according to the invention can be used successfully against phytopathogenic fungi, which adhere to the seeds, such as, e.g., *Tilletia tritici, Fusarium nivale* and types of helminthosporium.

The active ingredients according to the invention are suitable, without their field of application being in any way limited thereto, e.g., for use in viniculture, horticulture, especially the cultivation of vegetables and ornamental plants, for use on lawns, in the cultivation of rape, in hop growing, in strawberry plants and in the cultivation of malaceous fruits. The active ingredients according to the invention can, in addition, be used for the conservation of harvested fruit. A further field of application that has been found is their use as a seed-dressing agent.

The active ingredients according to the invention can be applied on their own or in admixture with other pesticidal, especially fungicidal, agents. Attention is drawn to active ingredient combinations with known botryticides for which resistance phenomena have already been observed.

Generally, the active ingredients according to the invention are used as mixtures with solid or liquid diluents or as solutions in solid or liquid solvents, with active ingredient contents of from 0.01 to 95% by weight.

The mixtures and solutions are manufactured, e.g., as emulsion concentrates, pastes, spray powders, granulates or microcapsules.

Emulsion concentrates and pastes contain generally from 10–60% by weight, preferably from 15–40% by weight, of active ingredient, from 2–25% by weight of dispersion auxiliaries and organic solvents and/or water.

Spray powders contain usually from 10–80% by weight, preferably from 15–70% by weight, of active ingredient, from 1–10% by weight of dispersion auxiliaries and from 10–89% by weight of inert constituents.

Granulates and dusting agents contain, in addition to inert constituents, binders and/or coating substances, from 1–10% by weight, especially from 5–10% by weight, of active ingredient.

The above are employed in accordance with the invention as follows:

(1) as dispersion auxiliaries, e.g., alkyl and aryl sulfonates, methyl cellulose, polymeric sulfonic acids and the salts thereof, polyalcohols, fatty acid esters, fatty alcohol ethers, and fatty amines;

(2) as organic solvents, e.g., alcohols (e.g., ethanol and butanols), dimethylformamide, dimethyl sulfoxide, N-methylpyrrolidone and aromatic substances (e.g., toluene and xylenes);

(3) as inert constituents, e.g., kaolin, china clay, talcum, calcium carbonate, highly disperse silica, silica gels, kieselguhr, diatomaceous earth, pumice, crushed maize, thickening agents, e.g., starch and carboxymethylcellulose; and (4) as binders, e.g., magnesium sulfate, gypsum, gum arabic.

The active ingredients according to the present invention are formulated, e.g., as follows:

1. Emulsion concentrate:
    20% by weight of active ingredient
    10% by weight of customary commercial epoxylated anhydrosorbitol monolaurate (trademark "Tween Twenty")
    70% by weight of dimethylformamide
2. Spray powder:
    20% by weight of active ingredient
    5% by weight of ammoniumlignin sulfonate (trademark "Totanin")

10% by weight of sodium oleylmethyl tauride (trademark "Arcopon T KONZ")

65% by weight of kaolin

The amounts of active ingredients used can vary widely. The amount of active ingredient required for the treatment of seeds is generally from 0.05 to 25 g/kg of seed.

The application of the active ingredients according to the invention can be effected in any suitable form. There may be mentioned by way of example, e.g., pouring, squirting, spraying, dusting, coating, and treatment of the seeds (dressing).

In the following examples, compositions of the present invention and their manufacture will be more fully described. However, it should be noted that these examples are given only by way of illustration and not of limitation.

EXAMPLE 1

Manufacture of 4-chlorophenyl-alpha-bromoacetic acid 3-iodopropargyl ester (a) 16 g (0.2 moles) of elemental bromine were added dropwise to 18.9 g (0.1 moles) of 4-chlorophenylacetic acid chloride at 95° C. while stirring. The reaction mixture was maintained for a further 2.5 hours at a temperature of 90° C. and then excess bromine was distilled off. The crude product was finally distilled under 16 mb in a temperature range of from 90° C. to 96° C. 22.9 g (0.085 moles) of 4-chlorophenyl-alpha-bromoacetic acid chloride, corresponding to 85% of the theoretical yield, were obtained.

(b) A solution of 8.04 g (0.03 moles) of 4-chlorophenyl-alpha-bromoacetic acid chloride (according to (a)) in 20 ml of absolute toluene was added dropwise, while stirring, to a solution of 5.46 g (0.03 moles) of 3-iodopropynol and 5 g of pyridine in 20 ml of absolute toluene. Subsequently, the reaction mixture was taken up in diethyl ether/water and finally the organic phase was separated off. The organic phase was extracted with 1N hydrochloric acid and then with saturated sodium bicarbonate solution. After drying with sodium sulfate and distilling off the solvent, 9.5 g (0.023 moles) of 4-chlorophenyl-alpha-bromoacetic acid 3-iodopropargyl ester remained, corresponding to 77% of the theoretical yield. The oil is characterized by the following NMR data:

$\delta$(80 MHz, CDCl$_3$)=4.81 (s, 2H); 5.26 (s,H)

7.21 (AB, J$_{AB}$=10 Hz, 2H)

7.34 (AB, J$_{AB}$=10 Hz, 2H) [ppm].

EXAMPLE 2

Manufacture of 2,4-dimethylphenylacetic acid iodopropargyl ester (a) Hydrogen chloride was introduced at 70° C. for 5 hours into a mixture of 106 g of m-xylene, 531 g of 16N hydrochloric acid and 39 g of paraformaldehyde. Subsequently, the organic phase was separated off and distilled. In the boiling range of from 96° C. to 100° C. at a pressure of 16 mb, 105 g (0.68 moles) of 2,4-dimethylbenzyl chloride, corresponding to 65% of the theoretical yield, were obtained.

(b) 10 g of tetrabutylammonium bromide were introduced, while stirring, into a mixture of 103 g (0.67 moles) of 2,4-dimethylbenzyl chloride (according to (a)) and 86 g (1.32 moles) of potassium cyanide in 50 ml of water. In the exothermic reaction, the reaction mixture warmed up to 60° C. Once the reaction had subsided, the organic phase was separated off and distilled. In the boiling range of from 86° C. to 91° C. at a pressure of 0.07 mb, 89 g (0.61 mole) of 2,4-dimethylbenzyl cyanide, corresponding to 94% of the theoretical yield, were obtained.

(c) 85 g (0.59 moles) of 2,4-dimethylbenzyl cyanide (according to (b)) were stirred at 150° C. for 5 hours in 50% by weight sulfuric acid. Subsequently, the reaction mixture was poured onto ice. The reaction mixture was then rendered alkaline with 2N sodium hydroxide solution and finally the aqueous phase was extracted with ether. After separating off the ethereal phase, the aqueous phase was acidified with 2N hydrochloric acid and the carboxylic acid resulting as precipitate was taken up in ether. After removing the ether, 69 g (0.42 moles) of 2,4-dimethylphenylacetic acid, corresponding to 71% of the theoretical yield, were obtained.

(d) A solution of 16.4 g (0.10 moles) of 2,4-dimethylphenylacetic acid (according to (c)) and 11 ml of thionyl chloride in 50 ml of cyclohexane was maintained at a temperature of 80° C. until the evolution of gas was complete. Subsequently, excess thionyl chloride was distilled off together with cyclohexane. The remaining acid chloride was dissolved in 20 ml of toluene and added dropwise to a mixture of 20.2 g (0.11 moles) of 3-iodopropynol and 15 g of triethylamine in 100 ml of toluene. The reaction temperature was 50° C. The reaction mixture was finally taken up in 100 ml of diethyl ether, then extracted with 1N hydrochloric acid and subsequently with saturated sodium bicarbonate solution. Finally, the phases were separated and the organic phase was dried with sodium sulfate. After distilling off the ether, 29.5 g (0.09 moles) of 2,4-dimethylphenylacetic acid iodopropargyl ester, corresponding to 90% of the theoretical yield, were obtained. Melting range 39°–40° C.

EXAMPLE 3

Manufacture of 2,6-dichloro-3-nitrophenylacetic acid iodopropargyl ester (a) While stirring, 29 g (0.14 moles) of 2,6-dichlorophenylacetic acid were introduced into a mixture of 40 ml of 80% by weight nitric acid and 20 ml of 96% by weight sulfuric acid. The reaction temperature was maintained in a range of from 0° to 5° C. After 1 hour, the reaction mixture was poured onto 400 g of ice. The desired product was obtained in the form of a precipitate, which was filtered off and washed with water until free of mineral acid. 32.3 g (0.13 moles) of 2,6-dichloro-3-nitrophenylacetic acid corresponding to 92% of the theoretical yield, were obtained.

(b) 15 g (0.06 moles) of 2,6-dichloro-3-nitrophenylacetic acid were suspended in 30 ml of cyclohexane and 20 ml of thionyl chloride. The whole was refluxed until the evolution of gas was complete. Subsequently, excess thionyl chloride and cyclohexane were distilled off. The resulting acid chloride was dissolved in 50 ml of absolute toluene and, while stirring, at a temperature of 30° C., added dropwise to a mixture of 11 g (0.06 moles) of 3-iodopropynol, 4.75 g of pyridine and 50 g of toluene. After 1 hour the reaction mixture was taken up in diethyl ether and the ethereal solution was extracted with 1N hydrochloric acid and then with saturated sodium bicarbonate solution. Finally, the organic phase was washed with water, dried with sodium sulfate and concentrated by evaporation. The crude product (22.7 g) was further purified by chromatography over silica gel. 15.5 g (0.037 moles) of 2,6-dichloro-3-nitrophenylacetic acid iodopropargyl ester corresponding to 63% of the theoretical yield, were obtained. Melting range 97°–99° C.

EXAMPLE 4

Manufacture of alpha-chlorophenylacetic acid iodopropargyl ester (a) 100 g (0.65 moles) of mandelic acid and 234 g (1.95 moles) of thionyl chloride were dissolved in 170 ml of cyclohexane and refluxed until the evolution of gas was complete. Subsequently, excess thionyl chloride and cyclohexane were distilled off. The crude product remaining was distilled by fractional distillation. In the boiling range of 103° to 109° C. at a pressure of 16 mb, alpha-chlorophenylacetic acid chloride was obtained in a yield of 75.7 g (0.40 moles), corresponding to 61% of the theoretical yield.

(b) 24.6 g of alpha-chlorophenylacetic acid chloride, dissolved in 20 ml of toluene, were added dropwise to a mixture of 23.7 g of 3-iodopropynol, 15 g of triethylamine and 100 ml of toluene. The reaction temperature was 60° C. The reaction mixture was finally taken up in 100 ml of ether and the ethereal solution was subsequently extracted first with 1N hydrochloric acid and then with saturated sodium bicarbonate solution. Finally, the organic phase was dried with sodium sulfate. After distilling off the ether, 36.5 g, corresponding to 84% of the theoretical yield, of alpha-chlorophenylacetic acid iodopropargyl ester were obtained.

The product is characterized by the following NMR data:

α-chlorophenylacetic acid iodopropargyl ester.

δ(80 MHz, CDCl$_3$)=4.81 (s, 2H); 5.31 (s, 1H) 7.1–7.5 (m,5H).

EXAMPLE 5

Spore Germination Test

50 μl of a solution or suspension of an active ingredient according to the invention together with 50 μl of a spore suspension produced by washing spores of an agar culture with a nutrient solution that contained per liter 10 g of sugar, 1 g of glycol, 1 g of KH$_2$PO$_4$ and 0.5 g of MgSO$_4$ were introduced into the concave-ground portion of concave-ground microscope slides.

The microscope slides were stored at 20° C. for 48 hours in a Petri dish, the base of which was covered with a moistened filter paper.

Subsequently, the ratio of germinated and non-germinated spores was compared with an untreated control specimen.

The degree of activity was calculated as a percentage in accordance with the following formula:

$$100 - \frac{\text{number of germinated spores, treated}}{\text{number of germinated spores, untreated}} \times 100$$

The following were used as active ingredients:
A 4-chlorophenylacetic acid iodopropargyl ester
B α-bromo-(4-chlorophenyl)-acetic acid iodopropargyl ester
C 2,6-dichlorophenylacetic acid iodopropargyl ester
D α-chlorophenylacetic acid iodopropargyl ester
E 2,4-dichloro-5-nitrophenylacetic acid iodopropargyl ester
F 4-nitrophenylacetic acid iodopropargyl ester
G 2,4-dichloro-3,5-dinitrophenylacetic acid iodopropargyl ester
H 4-chloro-3,5-dinitrophenylacetic acid iodopropargyl ester
V phenylacetic acid iodopropargyl ester as a comparison substance according to the state of the art.

The results are shown in Table 1:

TABLE 1

| | | Fungal toxicity with respect to fungal spores | | | | | | |
|---|---|---|---|---|---|---|---|---|
| Active Ingredient | Concentration of active ingredient in ppm | Alternaria tenuis | Botrytis cinerea | Fusarium culmorum | Fusarium nivale | Colletotrichum coffeanum | Verticillium dahliae | Penicillium glaucum |
| A | 4 | 90 | 90 | 95 | 90 | 95 | 95 | 95 |
|   | 2 | 80 | 80 | 95 | 80 | 90 | 80 | 95 |
|   | 1 | 80 | 80 | 90 | 60 | 80 | 80 | 90 |
| B | 4 | 100 | 100 | 100 | 100 | 100 | 100 | 100 |
|   | 2 | 100 | 100 | 100 | 100 | 100 | 100 | 100 |
|   | 1 | 100 | 100 | 100 | 100 | 100 | 100 | 100 |
| C | 4 | 95 | 100 | 95 | 100 | 95 | 100 | 90 |
|   | 2 | 95 | 95 | 95 | 100 | 95 | 100 | 90 |
|   | 1 | 95 | 95 | 95 | 100 | 95 | 100 | 60 |
| D | 4 | 90 | 90 | 95 | 90 | 95 | 95 | 95 |
|   | 2 | 90 | 80 | 95 | 80 | 90 | 80 | 95 |
|   | 1 | 80 | 80 | 90 | 60 | 80 | 80 | 90 |
| E | 4 | 100 | 40 | 100 | 100 | 100 | 40 | 100 |
|   | 2 | 100 | 30 | 100 | 100 | 100 | 30 | 100 |
|   | 1 | 100 | 30 | 100 | 100 | 100 | 30 | 100 |
| F | 2 | 100 | 40 | 40 | 80 | 90 | 90 | 80 |
| G | 2 | 70 | 100 | 70 | 80 | 60 | 70 | 70 |
| H | 2 | 100 | 70 | 90 | 90 | 100 | 40 | 100 |
| V | 4 | 100 | 50 | 40 | 90 | 80 | 30 | 40 |
|   | 2 | 90 | 0 | 0 | 70 | 30 | 0 | 0 |
|   | 1 | 80 | 0 | 0 | 60 | 20 | 0 | 0 |

A comparison of the results achieved with active ingredients according to the present invention with those of the comparison substance (V) demonstrates the increased fungicidal activity (e.g., against *Botrytis cinerea*) and, especially, a clearly broadened spectrum of activity.

EXAMPLE 6

Fungicidal activity against *Botrytis cinerea* in broad beans

Broad beans of the "Midget" variety were grown to a height of approximately 10 cm. The plants were sprayed until dripping wet with spray liquors containing 500 ppm of active ingredient.

When the spray coating had dried, the plants were inoculated with a spore suspension of *Botrytis cinerea*. The plants were placed in a climatic cabinet at a constant 20° C. and an atmospheric humidity of 95%.

After 6 days, fungicidal activity was evaluated. The activity was ascertained in comparison with untreated specimens.

The degree of activity as a percentage was ascertained in accordance with the following formula $$\% = \left(1 - \frac{\text{area attacked, treated}}{\text{area attacked, untreated}}\right) \times 100$$

The following were used as active ingredients:
I 2-chloro-3,5-dinitrophenylacetic acid iodopropargyl ester
K 2,6-dichloro-3,5-dinitrophenylacetic acid iodopropargyl ester
L 2,4,6-trimethylphenylacetic acid iodopropargyl ester
H 4-chloro-3,5-dinitrophenylacetic acid iodopropargyl ester
V phenylacetic acid iodopropargyl ester as a comparison substance according to the state of the art.

The results are compiled in Table 2:

TABLE 2

| Activity against *Botrytis cinerea* in broad beans at an active ingredient concentration of 500 ppm | |
|---|---|
| Active Ingredient | % Activity |
| I | 80 |
| K | 30 |
| L | 20 |
| H | 30 |
| V | 0 |

While only several embodiments and examples of the present invention have been shown and described, it is obvious that many changes and modifications may be made thereunto without departing from the spirit and scope of the invention.

What is claimed is:

1. A compound of the formula:

<chemical structure: phenyl ring with $X_n$ substituents, connected to $-CH(R)-C(=O)-O-CH_2-C\equiv CI$> wherein,
R represents a member selected from the group consisting of hydrogen, fluorine, chlorine, bromine, iodine, methoxy, 1-imidazolyl and 1,2,4-triazolyl;
X represents one or more of the same or different substituents independently selected from the group consisting of fluorine, chlorine, bromine, iodine, cyano, nitro, carboxyl, an alkyl of 1 to 12 carbon atoms, an alkoxy of 1 to 12 carbon atoms, a cycloalkyl of 3 to 6 carbon atoms, formyl, acetyl, propionyl, benzoyl, phenylsulfonyl, phenyl, phenoxy, and substituted phenyl and phenoxy each having from 1 to 3 substituents selected from the group consisting of fluorine, chlorine, bromine, nitro, methyl and methoxy; and
n is an integer of from 1 to 5 and, with the proviso that R does not represent hydrogen, n is 0 or an integer from 1 to 5.

2. The compound according to claim 1, wherein n is an integer from 1 to 5 and R is a member selected from the group consisting of hydrogen, chlorine and bromine.

3. The compound according to claim 1, wherein n is zero and R is a member selected from the group consisting of chlorine and bromine.

4. The compound according to claim 1, wherein n is an integer from 1 to 5 and X is a member selected from the group consisting of methyl, nitro, chlorine, bromine, iodine and methoxy.

5. The compound according to claim 1, wherein n is an integer from 1 to 4.

6. The compound according to claim 1, wherein n=1 with para- substitution of said selected X substituent.

7. The compound according to claim 1, wherein n=2, with o/p- substitution of said independently selected X substituents.

8. The compound according to claim 1, wherein n=2 with m/m'- substitution of said independently selected X substituents.

9. The compound according to claim 1, wherein n=2 with o/o'- substitution of said independently selected X substituents.

10. The compound according to claim 1, wherein n=3 with o/o'/p- substitution of said independently selected X substituents.

11. The compound according to claim 1, wherein n=3 with o/m/m'- substitution of said independently selected X substituents.

12. A fungicidal composition, comprising an effective amount of at least one active agent of the formula:

<chemical structure: phenyl ring with $X_n$ substituents, connected to $-CH(R)-C(=O)-O-CH_2-C\equiv CI$> wherein,
R represents a member selected from the group consisting of hydrogen, fluorine, chlorine, bromine, iodine, methoxy, 1-imidazolyl and 1,2,4-triazolyl;
X represents one or more of the same or different substituents independently selected from the group consisting of fluorine, chlorine, bromine, iodine, cyano, nitro, carboxyl, an alkyl of 1 to 12 carbon atoms, an alkoxy of 1 to 12 carbon atoms, a cycloalkyl of 3 to 6 carbon atoms, formyl, acetyl, propionyl, benzoyl, phenylsulfonyl, phenyl, phenoxy, and substituted phenyl and phenoxy each having from 1 to 3 substituents selected from the group consisting of fluorine, chlorine, bromine, nitro, methyl and methoxy; and
n is an integer of from 1 to 5 and, with the proviso that R does not represent hydrogen, n is 0 or an integer from 1 to 5.

* * * * *